(12) United States Patent
Giersch et al.

(10) Patent No.: US 10,507,052 B2
(45) Date of Patent: *Dec. 17, 2019

(54) SYSTEM FOR HANDLING AN AUGMENTATION IMPLANT

(71) Applicants: Woodwelding AG, Stansstad (CH); Stryker European Holdings I, LLC, Kalamazoo, MI (US)

(72) Inventors: Helge Giersch, Laboe (DE); Jörg Mayer, Niederlenz (CH); Andrea Müller, Winterthur (CH)

(73) Assignees: Woodwelding AG (CH); Stryker European Holdings I, LLC, Kalamazoo, MI (US)

( * ) Notice: Subject to any disclaimer, the term of this patent is extended or adjusted under 35 U.S.C. 154(b) by 343 days.

This patent is subject to a terminal disclaimer.

(21) Appl. No.: 15/342,560

(22) Filed: Nov. 3, 2016

(65) Prior Publication Data

US 2017/0100179 A1    Apr. 13, 2017

Related U.S. Application Data

(62) Division of application No. 14/381,355, filed as application No. PCT/EP2012/000880 on Feb. 29, 2012, now Pat. No. 9,510,886.

(51) Int. Cl.
*A61B 17/88* (2006.01)
*A61B 17/86* (2006.01)
(Continued)

(52) U.S. Cl.
CPC ...... *A61B 17/8822* (2013.01); *A61B 17/7098* (2013.01); *A61B 17/864* (2013.01);
(Continued)

(58) Field of Classification Search
CPC .............. A61B 17/864; A61B 17/8822; A61B 17/8833; A61B 17/8841
See application file for complete search history.

(56) References Cited

U.S. PATENT DOCUMENTS 4,154,239 A * 5/1979 Turley .............. A61M 37/0069
604/61
4,411,570 A    10/1983 Juric
(Continued)

FOREIGN PATENT DOCUMENTS

EP    2236101 A1    10/2010
FR    2445806 A1    8/1980
(Continued)

OTHER PUBLICATIONS

International Search report for Application No. PCT/EP2010/064542 dated May 31, 2011.
(Continued)

*Primary Examiner* — Samuel S Hanna
(74) *Attorney, Agent, or Firm* — Lerner, David, Littenberg, Krumholz & Mentlik, LLP

(57) ABSTRACT

A handling device for handling an augmentation implant is proposed, comprising an elongated housing having an axial through-bore for accommodating a sonotrode of an ultrasound applicator, and a lateral opening for inserting a pin magazine with an augmentation pin, wherein the axial through-bore and the lateral opening are connected to each other. The handling device further comprises a distal implant portion for fastening a proximal end of the augmentation implant at the housing, and a proximal tool portion for driving and/or augmenting the augmentation implant.

6 Claims, 8 Drawing Sheets

(51) Int. Cl.
*A61B 17/70* (2006.01)
*A61B 17/92* (2006.01)
*A61B 17/00* (2006.01)

(52) U.S. Cl.
CPC .......... *A61B 17/8875* (2013.01); *A61B 17/92* (2013.01); *A61B 17/8833* (2013.01); *A61B 17/8841* (2013.01); *A61B 2017/00004* (2013.01)

(56) References Cited

U.S. PATENT DOCUMENTS

| | | | |
|---|---|---|---|
| 4,428,261 | A | 1/1984 | Takatsu et al. |
| 4,475,266 | A | 10/1984 | Suska |
| 4,569,469 | A | 2/1986 | Mongeon et al. |
| 4,653,489 | A | 3/1987 | Tronzo |
| 4,929,239 | A | 5/1990 | Braun |
| 5,190,560 | A | 3/1993 | Woods et al. |
| 6,328,746 | B1 | 12/2001 | Gambale |
| 6,569,186 | B1 | 5/2003 | Winters et al. |
| 7,758,620 | B2 | 7/2010 | Porcher |
| 2004/0243139 | A1 | 12/2004 | Lewis et al. |
| 2005/0187559 | A1 | 8/2005 | Raymond et al. |
| 2006/0161161 | A1 | 7/2006 | Shifrin et al. |
| 2007/0260250 | A1 | 11/2007 | Wisnewski et al. |
| 2007/0265622 | A1 | 11/2007 | Aeschlimann et al. |
| 2007/0270833 | A1 | 11/2007 | Bonutti et al. |
| 2007/0271761 | A1 | 11/2007 | Haytayan |
| 2008/0262517 | A1 | 10/2008 | Wieland |
| 2009/0018590 | A1 | 1/2009 | Dorawa et al. |
| 2009/0088720 | A1 | 4/2009 | Oostman, Jr. |
| 2009/0163962 | A1 | 6/2009 | Dauster et al. |
| 2010/0076503 | A1 | 3/2010 | Beyar et al. |
| 2010/0256688 | A1* | 10/2010 | Giersch .................. A61B 17/68 606/305 |
| 2012/0143261 | A1* | 6/2012 | Giersch ................ A61B 17/864 606/304 |
| 2012/0283788 | A1* | 11/2012 | Wenger ............. A61B 17/7032 606/305 |

FOREIGN PATENT DOCUMENTS

| | | |
|---|---|---|
| WO | 0007510 A1 | 2/2000 |
| WO | 2007073743 A1 | 7/2007 |
| WO | 2008096363 A2 | 8/2008 |
| WO | 2009132472 A2 | 11/2009 |
| WO | 2011054122 A1 | 5/2011 |

OTHER PUBLICATIONS

International Written Opinion for Application No. PCT/EP2010/064542 dated May 31, 2011.
International Search Report and Written Opinion for Application No. PCT/EP2012/000880 dated Nov. 7, 2012.
Rea et al., "Bioactivity of ceramic-polymer composites with varied composition and surface topography", Journal of Materials Science: Materials in Medicine 15 (2004) 997-1005.
Bailey et al., "Biomechanical evaluation of a new composite bioresorbable screw", Journal of Hand Surgery (British and European Volume, 2006) 31 B: 2 : 208-212.
Fang et al., "Processing and mechanical ptoperties of HA/UHMWPE nanocomposites", Biomaterials Jul. 2006; 27(20):3701-3707.
Huang et al., "Syntheis and characterization of nano-HA/PA66 composites", Journal of Materials Science: Materials in Medicine 14(7):655-660, 2003
Bornfield et al., Materials World, vol. 5 No. 1:18-20, Jan. 1997.
Huang et al., "Novel Porous Hydroxyapatite Prepared by Combining H2O2 Foaming with PU Sponge and Modified with PLGA and Bioactive Glass", Journal of Biomaterials Applications; 21(4):351-374, Apr. 2007.
Juhasz et al., "Mechanical properties of glass-ceramic A-W-polyethylene composites: effect of filler content and particle size", Biomaterials, Mar. 2004, 25(6):949-955.

* cited by examiner

SYSTEM FOR HANDLING AN AUGMENTATION IMPLANT

CROSS-REFERENCE TO RELATED APPLICATIONS

This application is a divisional of U.S. application Ser. No. 14/381,355, filed on Nov. 20, 2014, which claims benefit of national phase entry under 35 U.S.C. § 371 of International Application No. PCT/EP2012/000880 filed Feb. 29, 2012, published as WO 2013/127406 A1, the disclosures of which are hereby incorporated herein by reference.

BACKGROUND OF THE INVENTION

The invention relates to a handling device for handling an augmentation implant. Furthermore, the invention relates to a corresponding method including driving in of the implant into an object and augmenting the same within the object. Known from U.S. Pat. No. 4,653,489 is a system wherein fixation cement is introduced through a screw into a portion of a bone afflicted by osteoporoses. Femoral neck fractures as well as distal femoral fractures can be fixated by means of this device.

The system in accordance with prior art comprises a screw having a flow cavity, i.e. an axial through-bore through which bone cement can be introduced into the portion at the tip of the screw. The bone cement is advanced by a device which is releasably attached to the subsequent end of the screw. This device is similar to commercially available syringes. In use of this prior art device, the fixation cement is injected in an already fluidized state into the axial through-bore of the screw. Due to the pressure, the fixation cement is adequately fluidized, so that it can pass through the proximal end of the screw into the bone, as a result of which the screw is augmented in the bone. This system has a drawback that the distribution of the fixation cement within the portion of the bone at the tip of the screw is neither reliable nor even.

SUMMARY OF THE INVENTION

WO 2011/054122 A1 describes a medical device which may be an augmentation implant or may be an augmentation device for strengthening human or animal hard tissue for subsequently implantation of a separate implant. The disclosure of this document is incorporated herein by reference.

An object of the invention may be to provide a device and a method by means of which a handling of an augmentation implant is facilitated. Another object may be to provide a device and a method by means of which a reliable and even augmentation of an augmentation implant in an installation site can be assured. This is achieved by the subject-matter of the respective independent claims. Further embodiments are described in the dependent claims.

According to an exemplary embodiment of the invention, a handling device for handling an augmentation implant comprises an elongated housing having an axial through-bore and a lateral opening in communication with each other, a distal implant portion and a proximal tool portion.

As used herein, in addition to the plain and ordinary meaning, the term "augmentation" can, for example, encompass any kind of anchoring. The term "augmentation" can, for example, encompass an anchoring by way of material which is arranged between an implant and an object, like a dowel between a screw and a wall. Furthermore, the term "augmentation" can, for example, encompass an anchoring by providing material which engages the implant as well as the surrounding tissue, but which material is introduced after the implant is inserted into the object. Consequently, an "augmentation implant" can be any kind of an implant which may be anchored by providing material between the implant and tissue surrounding the implant, i.e. which may be augmented. Accordingly, the overall volume of the augmentation implant is increased after the implant is inserted into tissue of an object, for example bone, wood or another porous material.

As used herein, in addition to the plain and ordinary meaning, the verb "to augment" can, for example, encompass any kind of anchoring or fixating of an implant in an object by providing material and thus increasing the overall volume of the implant, for example with a material which can be pressed from the implant into at least one cavity or into pores in tissue of an object, with the material being fluidized, wherein the material is capable of subsequently hardening. A material for augmenting an implant may be provided in form of an augmentation pin. An augmentation pin may be, for example, a small pin of approximately 3 cm to 4 cm, length with a few millimeters in diameter. It will be understood, that the dimensions of the augmentation pin depend upon the intended application, i.e. depends on the amount of material which is needed for a reliable augmentation of a particular implant. It is noted, that the material of the augmentation pin may be a polymer material being fluidizable and biocompatible, wherein a biocompatible material may be a material which does not negatively interfere with human or animal tissue. Additionally, the material may also be bioabsorbable.

In this text the expression "polymer material being fluidizable e.g. by mechanical vibration" or in short "fluidizable polymer material" or "fluidizable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration may be between 2 kHz and 200 kHz, preferably 20 to 40 kHz and the amplitude between 1 µm and 100 µm, preferably around 10 to 30 µm. Such vibrations may be e.g. produced by ultrasonic devices as e.g. known for dental applications. For being able to constitute a load-bearing connection to the tissue, the material at the time of insertion may have an elasticity coefficient of more than 0.5 GPa, preferably more than 1 GPa. The elasticity coefficient of at least 0.5 GPa also ensures that the fluidizable or liquefiable material may be capable of transmitting the ultrasonic oscillation with such little damping that inner fluidization or liquefaction and thus destabilization of the liquefiable element does not occur, i.e. liquefaction occurs only where the liquefiable/fluidizable material is at the liquefaction interface to the stop face. The plastification temperature is preferably of up to 200° C., between 200° C. and 300° C. or even more than 300° C. Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suitable thermoplastic material include any one of the polylactide products LR708 (amorphous Poly-L-DL lactide 70/30), L209 or L210S by Bohringer Ingelheim. Specific embodiments of degradable materials are Polylactides like LR706 PLDLLA 70/30, R208 PLDLA 50/50, L210S, and PLLA 100% L, all of Bohringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 Apr.;31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Hochst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The fluidizable/liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. The material of the liquefiable element(s), i.e. of an augmentation pin, may contain an additional substance, for example for promoting healing or regeneration of for furthering x-ray visibility. For example, the additional substance may be a growth factor, an antibiotic, an inflammation inhibitor or a buffer. More particularly, the additional substance be a drug promoting healing, in particular growth, differentiation and/or regeneration such as a proteinaceous drug like a growth and/or differentiation factor, e.g. of the Bone Morphogenic Protein family (especially BMP 2, 6, 7, for certain applications also BMP 12, 13), an Insulin Growth Factor (e.g. IGF 1), a Platelet Derived Growth Factor (PDGF), a Growth and Differentiation Factor (e.g. GDF 5) etc. and also combinations thereof and/or other another drug including a non-proteinaceous drug including small molecules (e.g. biphosphonates), possibly in combination with a proteinaceous drug, etc.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non-degradable polymers include: Bioglasses, Hydroxyapatite (>90% crystallinity), HAPEX®, see S M Rea et al., J Mater Sci Mater Med. 2004 Sept.; 15(9):997-1005; for hydroxyapatite see also L. Fang et al., Biomaterials 2006 Jul.; 27(20):3701-7, M. Huang et al., J Mater Sci Mater Med 2003 Jul.; 14(7): 655-60, and W. Bonfield and E. Tanner, Materials World 1997 Jan.; 5 no. 1:18-20. Embodiments of bioactive fillers and their discussion can for example be found in X. Huang and X. Miao, J Biomater App. 2007 Apr.;21 (4):351-74), J A Juhasz et al. Biomaterials, 2004 Mar.; 25(6):949-55. Particulate filler types include: coarse type: 5-20 μπι (contents, preferentially 10-25% by volume), sub-micron (nano-fillers as from precipitation, preferentially plate like aspect ratio >10, 10-50 run, contents 0.5 to 5% by volume).

A specific example of a material with which experiments were performed was PLDLA 70/30 comprising 30% (weight percent) biphase Ca phosphate that showed a particularly advantageous liquefaction behaviour.

The material of the sheath element (which may be a screw, especially pedicle screw) may be any material that does not melt at the melting temperatures of the liquefiable material. Especially, the sheath element may be of a metal, for example a titanium alloy. A preferred material is titanium grade 5. This material, in addition to being generally suited for implantable devices, has a comparably low heat conduction. Because of this low heat conduction, the melting zone arising in liquefiable material and at the interface to the directing structure is heated quickly, without the surroundings being heated to too high temperatures. Alternative materials for the sheath element are other metals like other titanium alloys, stainless steel, ceramics like Zirconium oxides or Aluminum oxides, or hard plastics such as PEEK etc.

An augmentation pin may or may not include a closing plug, wherein the closing plug may be fixedly attached to a leading end of a pin made of augmentation material or may be provided as a separate element so that a combination of a closing plug with a pin made of augmentation material may be formed within an augmentation implant by inserting firstly the closing plug and secondly the pin. An augmentation pin may be inserted through the lateral opening of the elongated housing of the handling device according to the invention so that the augmentation pin is aligned with the axial through-bore, and may be pushed for example by a sonotrode of an ultrasound applicator through the axial through bore in a direction to the distal implant portion. At the distal implant portion a proximal end of an augmentation implant may be coupled to the elongated housing, wherein the augmentation implant may be provided with an axial bore so that the augmentation pin may be pushed out of the distal implant portion and into the axial bore in the augmentation implant.

For example, the augmentation implant may be an augmentation screw, wherein the augmentation material may be pressed from the inside of the screw to the outside so as to surround at least partially the outer thread of the screw. According to another example, the augmentation implant may be any kind of nail or bolt the outer surface of which is not provided with a thread, but which may be provided with ribs or protrusions, thus being also non-circular. It is noted, that the augmentation implant may also be a plate for stabilizing for example a fractured object at an outer surface thereof, wherein additional material may be provided so as to extend from the plate into at least one cavity formed in the object beneath the plate.

The proximal tool portion of the elongated housing of the handling device is designed so that the augmentation implant can be easily handled by means of the handling device, i.e. can be held and accurately positioned at an installation site at an object and/or can be driven in into the object. In other words, the proximal tool portion may serve as a grip of a screwdriver or as a grip for holding the handling device and thus an augmentation nail while punching the nail into an object.

According to an embodiment of the invention, the handling device further comprises an ultrasound applicator having an ultrasound transducer and a sonotrode, wherein the ultrasound applicator is arranged so that the sonotrode extends from the ultrasound transducer in a direction toward the distal implant portion. The ultrasound applicator may be capable of fluidizing the material of the augmentation pin within the augmentation implant by means of a combination of pressure and ultrasound vibrations, and pressing the fluidized material through at least one bore out of the implant. It will be understood that at least the sonotrode of the ultrasound applicator is movably arranged to be capable of pushing an augmentation pin through the elongated housing and of pressing the material of the augmentation pin out of the implant when the material of the augmentation pin is fluidized.

According to an embodiment of the invention, the ultrasound applicator may be integrated into the proximal tool portion of the handling device.

According to a further embodiment of the invention, the proximal tool portion may be adapted for releasably connecting the ultrasound applicator at the elongated housing. In this case, the handling device may further comprise a driving tool with a distal driving end, wherein the distal driving end is adapted to be coupled at the proximal tool portion when the ultrasound applicator is released from the proximal tool portion. For example, the driving tool may be an active screwdriver providing appropriate torque wherein the active screwdriver may be driven electrically, pneumatically or hydraulically. According to another embodiment, the distal implant portion of the handling device, i.e. the connection between the distal implant portion and the augmentation implant, is adapted to transmit forces from the elongated housing to the augmentation implant, for driving in the augmentation implant into an object, wherein these forces may be rotational forces or translational forces as well as a combination thereof, depending on the kind of the implant.

The distal implant portion of the handling device may include a quick-fastener.

In accordance with a further embodiment, the handling device may further comprise a locking element for blocking a lateral movement of the augmentation pin, when the augmentation pin is placed in the lateral opening and is aligned with the axial through-bore. The functionality of the handling device may be further enhanced in that the lateral opening of the elongated housing is a through-opening and a projection projects into the lateral opening, so that the augmentation pin is automatically aligned with the axial through-bore, when the augmentation pin is placed in the lateral opening and abuts the projection.

According to yet another embodiment, the handling device may further comprise a pin-magazine, wherein at least one pin-retainer may be provided in that pin magazine for holding at least one augmentation pin. The pin-magazine may be adapted to be placed in the lateral opening of the housing and may be adapted to align the augmentation pin with the axial through-bore in the housing, so that the augmentation pin may be inserted into an augmentation implant.

It will be understood that the pin-magazine may be designed corresponding to the shape of the lateral opening in the housing of the handling device in order to be placed in the lateral opening only with a specific orientation and direction.

In accordance with a further embodiment of the invention, the handling device is adapted to augment an implant by means of a plurality of augmentation pins, wherein these pins may be provided in one pin magazine. Each of the augmentation pins may be pushed from the elongated housing into an augmentation implant by means of the sonotrode of the ultrasound applicator. For this, the ultrasound applicator may be movable between a first position and a second position. The distal tip of the sonotrode may be located proximal to the lateral opening, i.e. the location at which an augmentation pin can be inserted into the elongated housing, when the ultrasound applicator is in the first position. On the other hand, the distal tip of the sonotrode may be located at or beyond the distal implant portion, i.e. within an augmentation implant, when the ultrasound applicator is in the second position. Accordingly, the sonotrode may be capable of pushing an augmentation pin from the lateral opening through the axial through bore and into the augmentation implant.

According to an embodiment, the sonotrode of the ultrasound applicator may include a section with reduced diameter. In a case in which an augmentation pin is provided in a pin magazine, the sonotrode will extend more or less through the pin magazine, when the sonotrode has pushed the augmentation pin to the distal implant portion of the handling device and into an augmentation implant. The section with reduced diameter is adapted so as to ensure that there is no contact between the shaft of the sonotrode and the pin magazine, when ultrasound vibrations are transmitted by the sonotrode. By way of this, any loss of transmitted energy can be avoided during the fluidization and pressing out of the material of the augmentation pin.

According to a further embodiment, a kit may be provided including a handling device as described above together with an augmentation implant.

A description in more detail of the steps performed while using the handling device in accordance with the invention may be followed in conjunction with the detailed description of an exemplary embodiment below.

It has to be noted that embodiments of the invention are described with reference to different subject-matters. In particular, some embodiments are described with reference to method-type claims, whereas other embodiments are described with reference to apparatus-type claims, however, a person skilled in the art will gather from the above and the following description that, unless otherwise notified, in addition to any combination of features belonging to one type of subject-matter, also any combination of features relating to different subject-matters is considered to be disclosed with this application. These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

Figure 1:
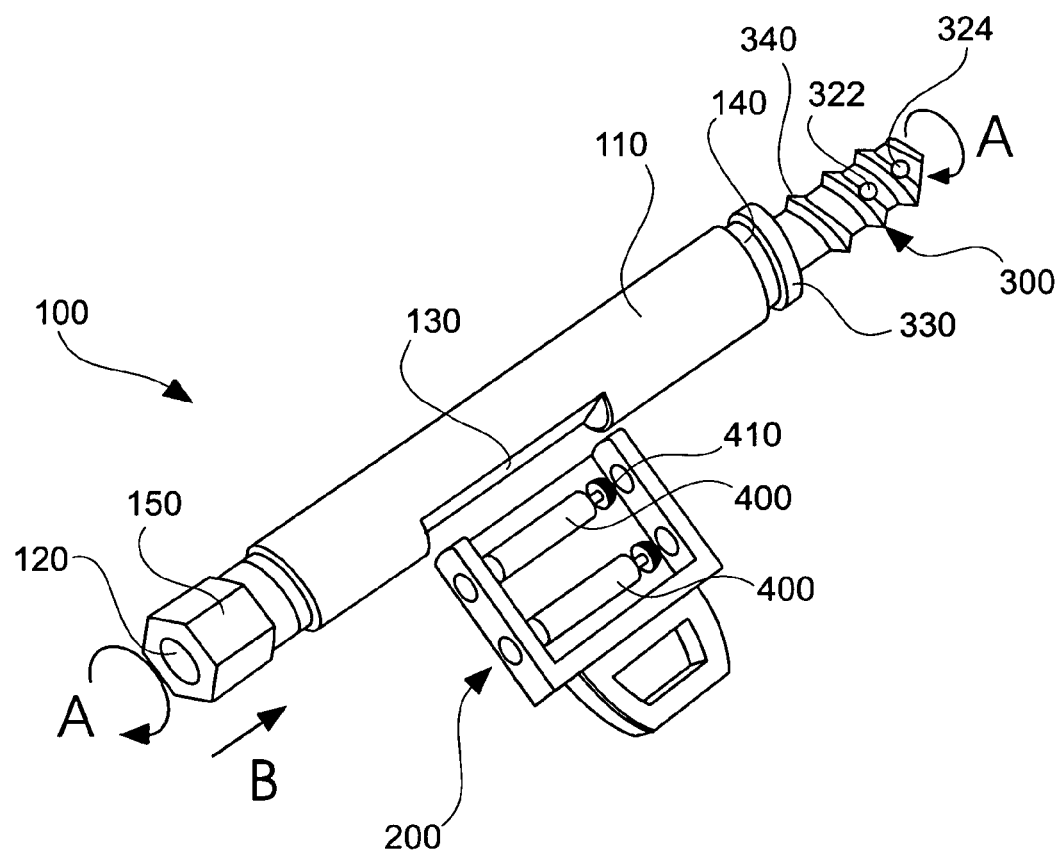
FIG. 1 is a schematically illustration of an exemplary handling device according to the invention.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION OF EXEMPLARY EMBODIMENTS

FIG. 1 provides an isometric illustration of the handling device 100 according to an exemplary embodiment of the invention, including an elongated housing 110, an axial through-bore 120, a lateral opening 130, a distal implant portion 140, and a proximal tool portion 150.

The lateral opening 130 is asymmetrically shaped to assure that a pin-magazine 200 which may be correspondingly formed, can be inserted into the lateral opening 130 only in one predetermined way. In the pin magazine 200, two augmentation pins 400 are shown, wherein each of the augmentation pins comprises a closing plug 410 arranged at the leading end of the pin. Each of the augmentation pins can be inserted into the elongated housing 110 so that the closing plug rests within the axial through-bore 120 at a predetermined position allowing the material of the augmentation pin to flow out of a predetermined lateral bore 322 and/or 324, when fluidized.

It is noted, that the pin-magazine may be a rotary cylinder with augmentation pins arranged like bullets in a revolver, instead of the straight and flat pin-magazine shown in the figures.

Further shown in FIG. 1 is an augmentation screw 300 the proximal end portion 330 being connected to the distal implant portion 140 of the handling device 100. The augmentation screw comprises an outer thread 340, wherein two lateral bores 322, 324 are formed in the portion of the outer thread. The lateral bores are provided with a different distance to the distal tip of the augmentation screw 300.

As indicated by the arrows A and B, appropriate rotational and translational forces can be applied on the augmentation screw 300 by means of the handling device 100.

Figure 2:
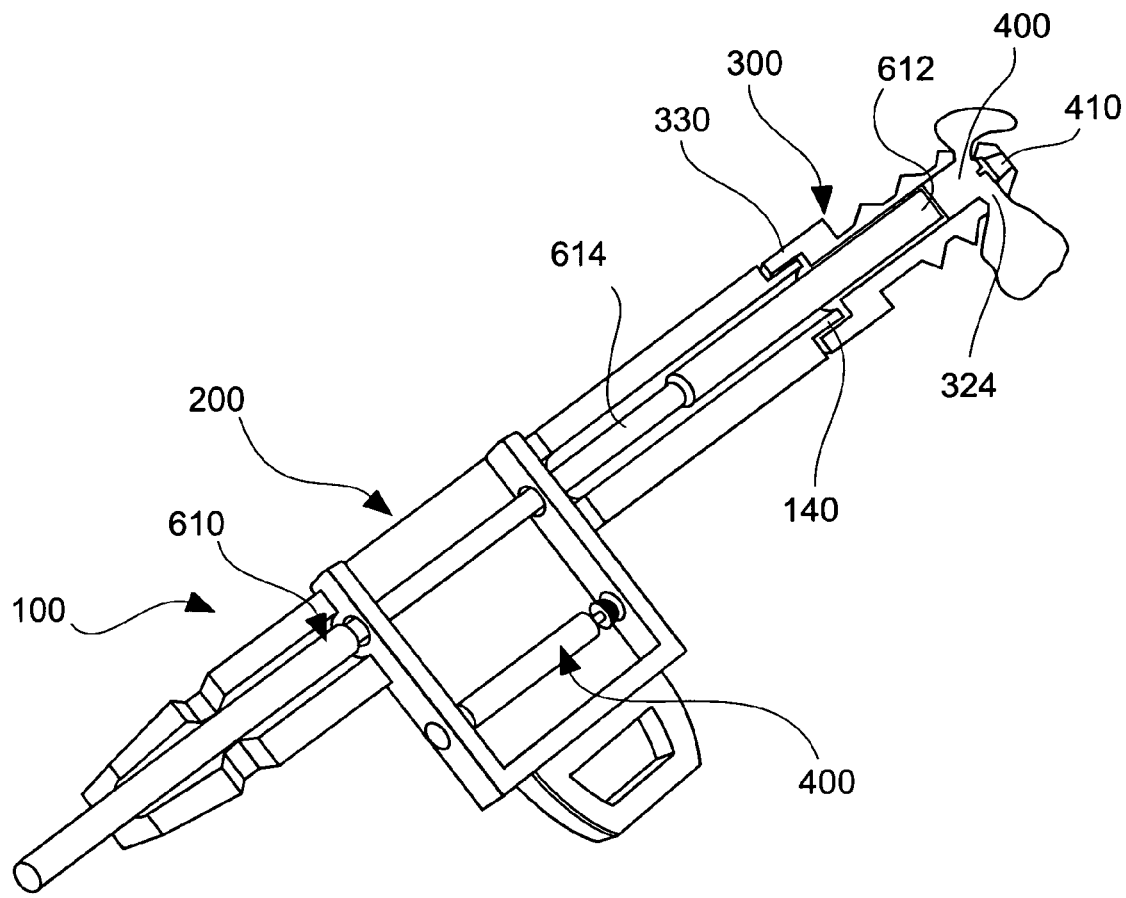
FIG. 2 is a sectional view of an exemplary handling device according to the invention.

FIG. 2 is a sectional side view of the handling device 100 together with a pin magazine 200 and an augmentation screw 300. FIG. 2 illustrates a situation in which a first augmentation pin 400 is pushed by means of a sonotrode 610 out of the pin magazine 200 and into the augmentation screw 300, and is already fluidized and pressed through lateral bores 324 out of the augmentation screw 300.

The sonotrode as shown in FIG. 2 comprises a tip 612 and a section 614 with reduced diameter. The section 614 has a length which is sufficient to ensure that the sonotrode shaft will be not in contact with the pin magazine 200 when the sonotrode tip 612 fluidizes an augmentation pin 400 in an augmentation screw 300, wherein the closing plug 410 prevents any flowing out of fluidized material out of the augmentation screw 300 in an axial direction.

Further schematically illustrated in FIG. 2, is a connection between a distal implant portion 140 of the handling device 100 and the proximal portion 330 of the augmentation screw 300, with the distal implant portion 140 engaging inside the proximal portion 330.

Figure 3:
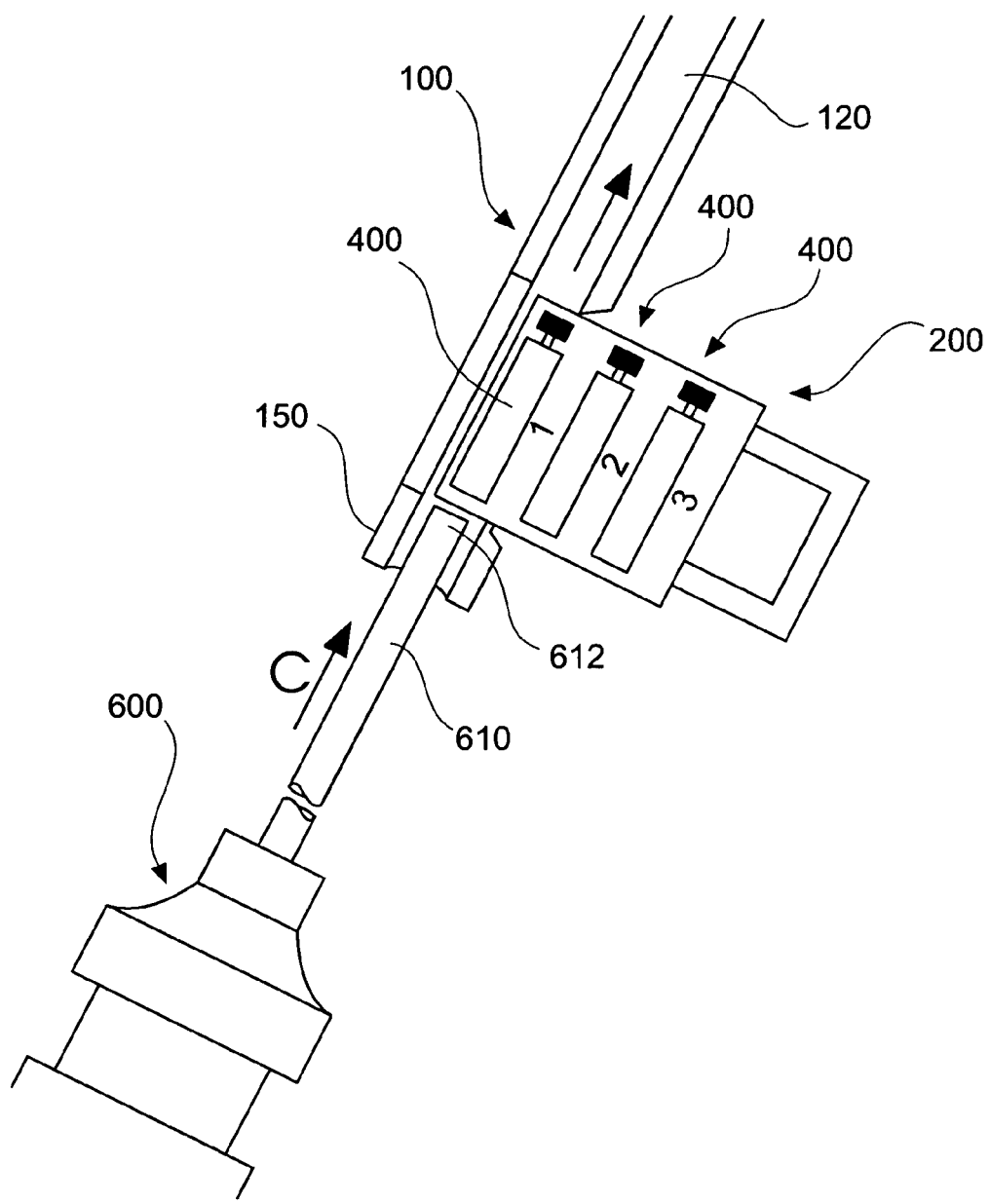
FIG. 3 is an illustration of an exemplary handling device with an ultrasound applicator being releasably connected to the elongated housing.

FIG. 3 illustrates an exemplary embodiment within ultrasound applicator 600 which can be releasably coupled to the proximal tool portion 150 of the handling device 100. A sonotrode 610 protrudes from the housing of the ultrasound applicator so that the sonotrode 610 can be introduced into the axial through bore 120 in the proximal tool portion 150, can be moved through the axial through bore 120 until then tip 612 is in contact with a augmentation pin 400 to push the augmentation pin 400 in a direction to the distal implant portion of the augmentation handling device 100 when the sonotrode 610 is further moved through the axial through bore 120.

The length of the sonotrode 610 may be adapted so that the augmentation pin 400 is located within an augmentation implant and at the same time the housing of the ultrasound applicator 600 can be coupled to the proximal tool portion 150 of the handling device 100.

Figure 4A:
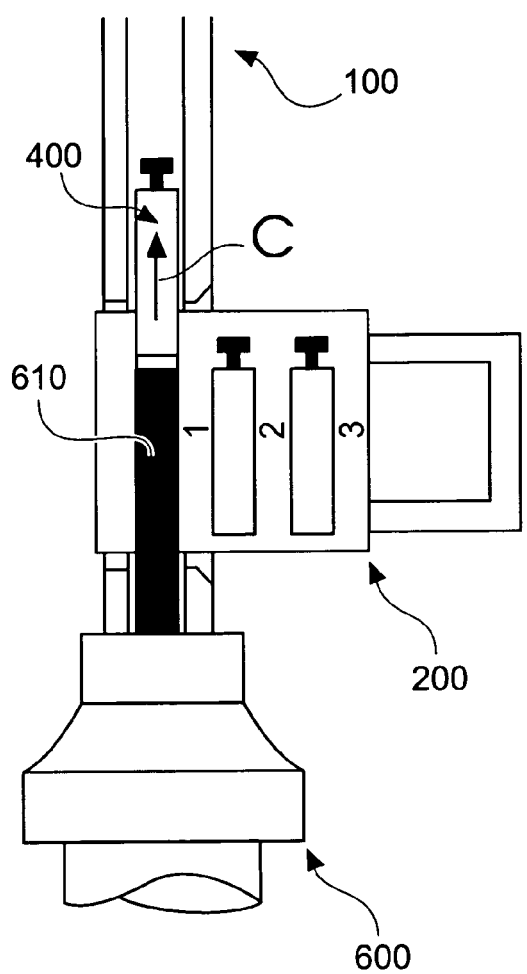
FIGS. 4a and 4b are illustrations of an exemplary handling device with an ultrasound applicator being fixedly connected to the elongated housing.
Figure 4B:
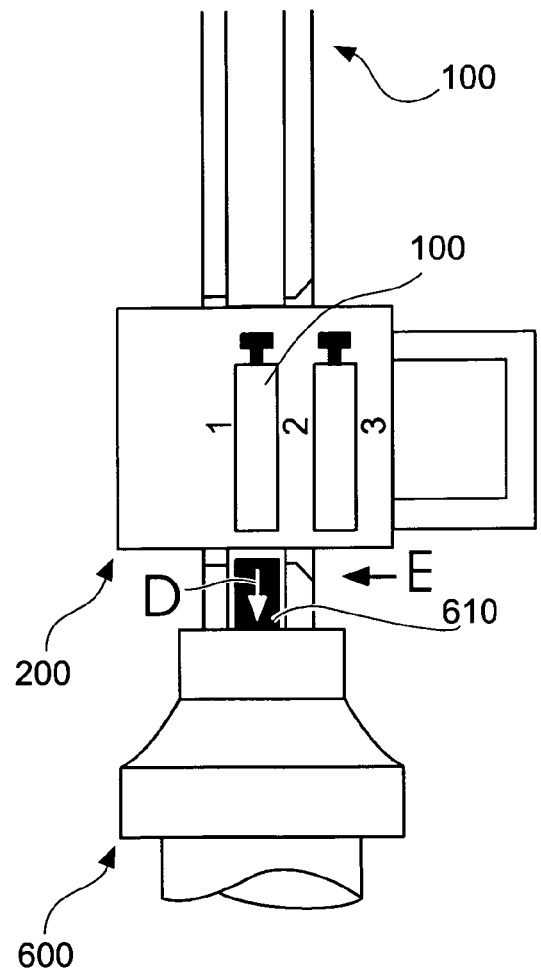
Figure 5:
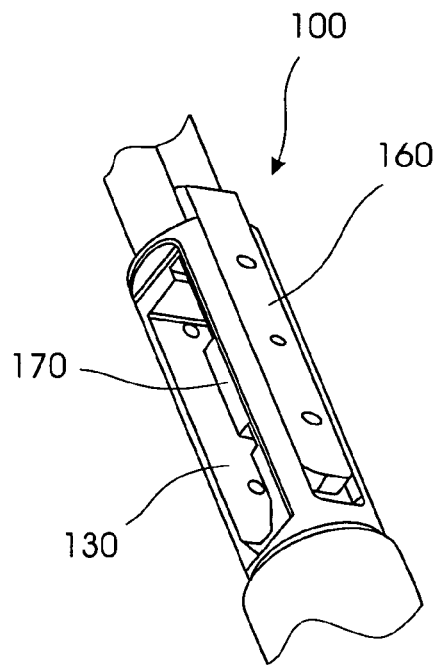
FIG. 5 is a detail view of the lateral opening in the elongated housing.

FIGS. 4a and 4b show another exemplary embodiment in which the housing of the ultrasound applicator 600 can be fixedly connected to the proximal tool portion of the handling device 100. In this case, the sonotrode 610 may be movable within the housing of the ultrasound applicator. Thus, the sonotrode 610 can be moved in a direction to the distal implant portion (arrow C) so as to push an augmentation pin 400 to and into an augmentation implant, as shown in FIG. 4a. After fluidizing a first augmentation pin, the sonotrode 610 can be pulled back (arrow D) so that the tip of the sonotrode 610 is located proximal to the lateral opening, i.e. proximal to the pin magazine 200, as shown in FIG. 4b. Then, the pin magazine 200 can be further inserted (arrow E) until a second augmentation pin 400 is aligned with the axial through bore of the handling device 100. FIG. 5 shows an exemplary embodiment of the handling device 100 including a locking element 160 as well as a projection 170.

The locking element 160 may include at least one locking pin (not shown) which protrudes into the lateral opening 130 and which is adapted to engage for example in a notch 240 formed at a pin-magazine 200 to lock the pin-magazine within the lateral opening. Further the locking element 160 may include a resilient element (not shown) for biasing the locking element 160 in a locking position. That is, a pin-magazine 200 may only be inserted into the lateral opening 130, when the locking element 160 is moved against the force of the resilient element, for example by hand or by a structural element at the pin-magazine, when the pin-magazine is inserted into the lateral opening. The locking pin may engage into the notch in the pin-magazine, when the locking element 160 is released. This will result in a locked positioning of the pin-magazine in the housing of the pin-inserter. The projection 170 which is shown in accordance with this embodiment, projects from one side into the lateral opening 130. The projection 170 may be a substantially flat element, which provides an abutment for an augmentation pin, so that the augmentation pin will be reliably aligned with the axial through-bore in the elongated housing, when the augmentation pin abuts at the projection 170.

Figure 6:
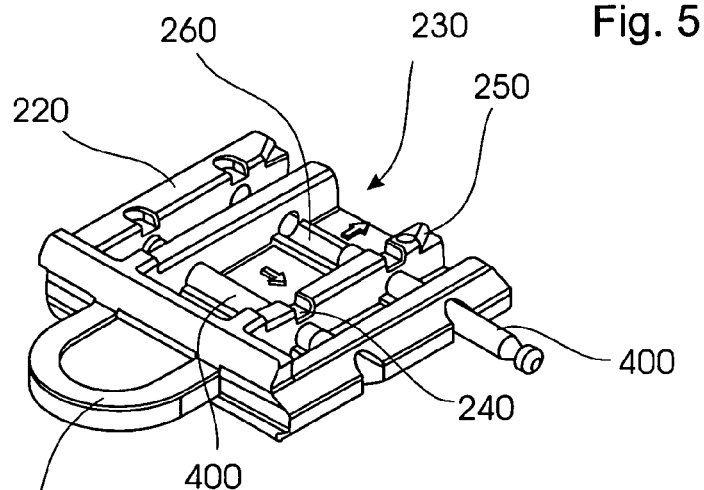
FIG. 6 is a detail view of an exemplary pin magazine.

FIG. 6 shows an exemplary embodiment of a pin-magazine 200. The pin-magazine 200 includes a grip portion 210, a body 220, and a recess 230. Transverse to the grip portion 210, two pin-retainers 260 are formed. Each pin-retainer is realized by a sequence of recesses within and bores through the body 220 of the pin-magazine. A first pin-retainer is formed at a position away from the grip portion 210, and a second pin-retainer is formed nearby the grip portion 210.

By way of the distinct arrangement of the pin-retainers 260 relative to the grip portion 210, it can be assured, that the pin-magazine 200 will be inserted into the lateral opening 130 of the handling device in a correct way, when the pin-magazine 200 is gripped at the grip portion 210.

The recess 230 is formed in the pin-magazine 200 nearby or at the pin-retainers 260, so that on the one hand, when the pin-magazine is placed in the lateral opening of the housing, a projection 170 at the housing may protrude into the recess, and on the other hand, when the augmentation pin is located in the pin-retainer, a portion of the augmentation pin 400 is laterally exposed for an abutment at the projection. That is, an augmentation pin which is accommodated within the pin-retainer of the pin-magazine, may be easily handled and introduced from the side into the housing of the pin-inserter, wherein an abutment of the augmentation pin at a projection within the housing indicates the correct position of the pin-magazine as well as the augmentation pin inside the housing of the pin-inserter. An automatic alignment of the augmentation pin with the axial through-bore of the pin-inserter can thus be assured. In the body 220 of the pin-magazine 200, notches 240 may be formed, which are provided for an engagement with respective locking pins of the locking element 160 of the handling device. Such locking pins may be press to a side by means of chamfers 250 provided at the body 220, so that the locking element may be passively actuated when the pin-magazine is inserted into the lateral opening of the handling device. By way of this, the pin-magazine may be fixated at a predetermined position and it may be avoided that the pin-magazine falls accidentally out of the pin-inserter.

Further, signs like arrows may be provided at the body, indicating for example a direction for an insertion of the magazine into the pin-inserter, or numbers (shown in FIGS. 3, 4a, 4b) referring to the sequence for the augmentation pins.

In FIG. 6, also augmentation pins 400 are visualized within the pin-retainers 260, wherein one of the augmentation pins 400 is pushed half way out of the respective pin retainer 260.

An augmentation implant 300 which may be preferably used with a handling device 100 as described above, may comprise an axial bore for receiving an augmentation pin 400, the axial bore may include at least a first step between a first section with a first diameter and a second section with a second diameter, with the second diameter being greater than the first diameter. The augmentation implant may further comprise a second step between for example the second section and a third section with a third diameter, with the third diameter being greater than the second diameter. At the second section and adjacent the first step, at least one first lateral bore may be provided. At the third section and adjacent the second step, at least one second lateral bore may be provided. Depending on the diameter of the closing plug of the augmentation pin, the closing plug and thus the augmentation pin may rest on the first step or the second step, when inserted into the axial bore of the augmentation implant. Having two steps in the axial bore provides the advantage that such an implant may be utilized in different applications by use of different and/or additional augmentation pins. It will be understood, that also an augmentation implant with more than two steps may be provided if appropriate in a particular application.

Figure 7:
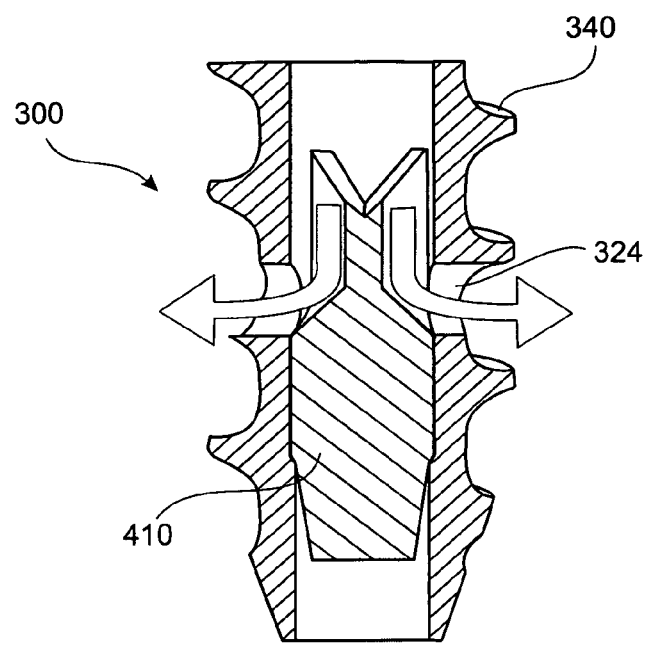
FIG. 7 is a sectional view of a leading end of an augmentation screw with a closing plug.

The augmentation implant may further comprise a portion with an outer thread, wherein the first lateral bore as well as the second lateral bore are located in that portion. FIG. 7 shows a distal portion of such an augmentation implant 300, i.e. an augmentation screw with at least first lateral bores 324 (two bores with the same distance from the distal end of the implant). A closing plug 410 is located within an axial through-bore of the augmentation screw and is closing the axial through-bore so that any fluidized material may be pressed only out of the lateral bores 324, as indicated by the arrows in FIG. 7.

Figure 8:
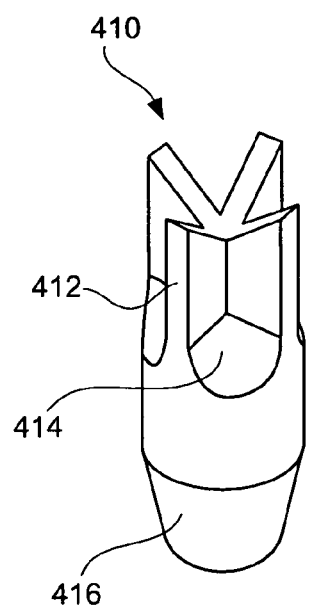
FIG. 8 is an isometrical illustration of a closing plug.

FIG. 8 shows an exemplary embodiment of a closing plug 410 comprising ribs 412 forming recesses 414 leading fluidized material to lateral bores, as shown in FIG. 7. Furthermore, the closing plug includes a tapered leading end portion 416 so that the closing plug will fixedly clamp at a step in an axial through-bore of an augmentation implant, as described above and shown in FIG. 7.

With a closing plug 410 as shown in FIGS. 7 and 8, it may be possible to utilize more than one augmentation pin made only by fluidizable material.

Furthermore, it may be possible to alternate such a closing plug with an augmentation pin made only by fluidizable material, i.e. inserting a closing plug without augmentation material and subsequently inserting a pin made of augmentation material. It will be understood that, in this case, the lateral bores may be provided at the augmentation implant with a distance in an axial direction, corresponding to the length of a closing plug so that with each further closing plug augmentation material may be pressed out of further proximally arranged lateral bores. According to another exemplary embodiment the closing plug is fixedly attached to the leading end of a pin like element made of fluidizable material.

In a case in which the augmentation implant includes at least two steps with different diameters, the pin-magazine may comprise two pin-retainers adapted to hold two augmentation pins with closing plugs having corresponding different diameters. With this particular embodiment, an augmentation of for example a screw fixating a femur nail may be realized in two or more steps. The difference of both plugs (and possibly pins) will be a diverse diameter in a range of a 10th of a millimeter. Since this diverse diameters are not directly visible, it is appropriate to use a pin magazine to separate the pins.

Since the pin-magazine may fit in a specific way into the lateral opening of the handling device, the two different pins located in the pin-retainers of the pin-magazine can only be introduced into the handling device in a predetermined sequence. Thus, no mistake is possible by inserting the pins.

Figure 9:
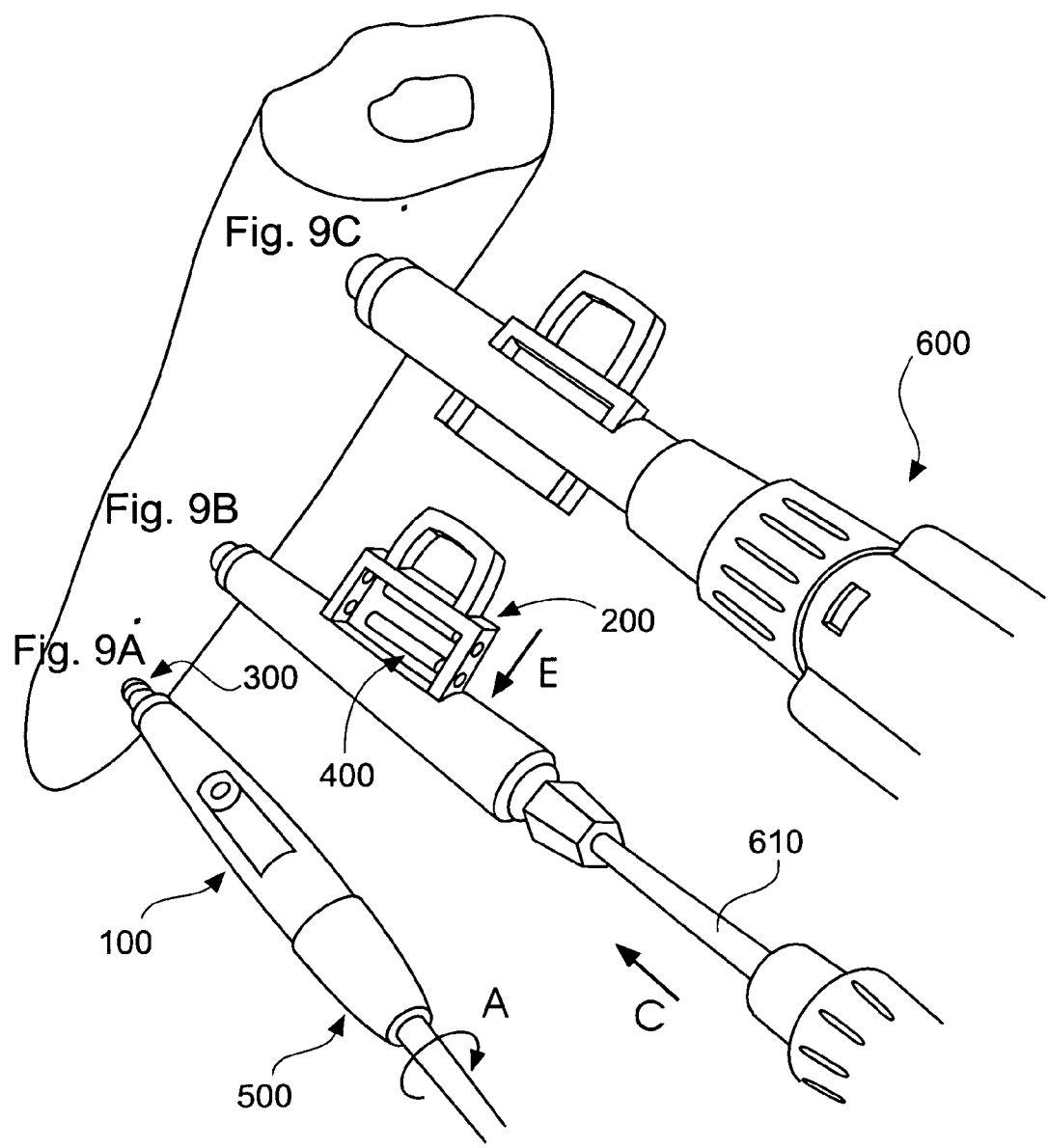
FIGS. 9A, 9B and 9C show a sequence illustrating the augmentation of an implant using a plurality of augmentation pins.

FIG. 9 illustrates an exemplary sequence of handling an augmentation screw.

In a first instance, shown down left in FIG. 9 A, and augmentation implant 300 is coupled to the distal implant portion of the handling device 100 and a driving tool 500 is releasably connected to the proximal tool portion of the handling device 100. As indicated by arrow A, torque is transmitted by the handling device 100 from the driving tool 500 to the augmentation implant 300 with the aim to insert the augmentation implant into an object.

In a second instance, shown in the middle in FIG. 9B, a pin magazine 200 is inserted into the handling device, as indicated by arrow E. With the pin magazine 200 inserted such that an augmentation pin 400 is aligned with the axial through bore in the handling device 100, an ultrasound applicator with the sonotrode 610 is inserted into the proximal tool portion and is capable of pushing the augmentation pin 400 out of the pin magazine and into the augmentation implant.

Figure 10:
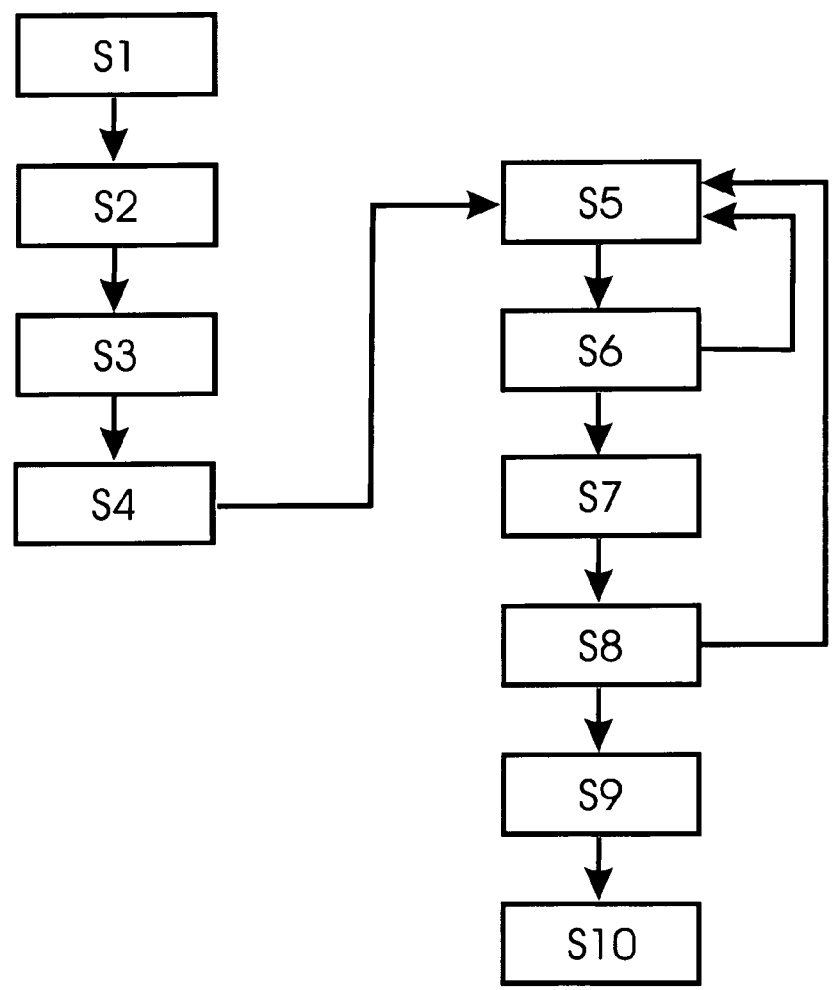
FIG. 10 is a flowchart representing method steps in accordance with the invention.

In a third instance, shown up right in FIG. 9C, the ultrasound applicator 600 is connected to the handling device and the pin magazine is fully inserted into the handling device. That is, a last of a plurality of augmentation pins is pushed into the augmentation implant and may be fluidized and pressed out of the augmentation implant so that the augmentation of the implant is completed. The flowchart in FIG. 10 illustrates the principles of using the handling device according to the invention, i.e. Illustrates the principles of handling and augmentation implant. It will be understood that the steps described with respect to the method, and also with respect to FIG. 9, are major steps, wherein these major steps might be differentiated or divided into several sub-steps. Furthermore, there might be also sub-steps between these major steps. Therefore, a sub-step is only mentioned if that step may be important for the understanding of the principles of the method according to the invention.

In step SI, in implant is connected to the distal implant portion of the handling device.

In step S2, a driving tool is connected to the proximal tool portion of the handling device.

In step S3, a force is applied to the implant via the handling device and thus the implant is introduced or implanted at an installation site. For example, it may be an augmentation screw which is implanted protruding through a transverse bore in a gamma nail.

In step S4, the driving tool is removed from the handling device.

In step S5, a pin-magazine with at least one augmentation pin is placed within the lateral opening of the housing of the handling device so that one augmentation pin is aligned with an axial through-bore in the handling device. This alignment may be achieved by an abutment of the augmentation pin at a projection protruding into the lateral opening in the housing of the handling device.

In step S6, an ultrasound applicator is connected to the proximal tool portion of the handling device. By introducing the sonotrode of the ultrasound applicator into the axial through bore of the elongated housing, the augmentation pin is pushed out of the pin-magazine, through the elongated housing of the handling device and into the augmentation implant. The length of the sonotrode fits to the distance between the proximal end of the housing of the handling device and the proximal end of the augmentation pin inside the augmentation implant.

According to an exemplary embodiment in which alternatingly a closing plug and a pin made only from fluidizable material, i.e. augmentation material, are inserted into the axial through-bore of the augmentation implant, steps S5 and S6 will be performed twice to achieve a combination of a closing plug and a pin made of augmentation material within the augmentation implant. It will be understood that, to achieve this, a pin magazine may be provided with a closing plug followed by a pin made of augmentation material, wherein the closing plug and the pin may be provided in separate retainers of the pin magazine. This case is indicated by the arrow going from step S6 back to step S5.

In step S7, ultrasonic vibrations together with a predetermined force is applied by the sonotrode to the augmentation material so that the material is fluidized and pressed out of at least one bore of the augmentation implant. In step S8, at least the sonotrode of the ultrasound applicator is pulled back to enable an insertion of a further augmentation pin aligned with the axial through bore in the handling device. If more than one augmentation pin, i.e. a combination of a closing plug and a pin made of augmentation material, should be utilized, the method steps S5 to S8 will be repeated, which is illustrated by the arrow going from step S8 back to step S5.

After the fluidization of all augmentation pins, in step S9, the ultrasonic applicator is removed from the proximal tool portion of the handling device.

In step S10, the handling device will be removed from the proximal end of the augmentation implant. It is noted, that steps S2, S4, S6 and S8 may be omitted in case of an exemplary embodiment in which the ultrasound applicator is integrated in the elongated housing and the proximal tool portion is adapted to be gripped so that the elongated housing serves as a driving tool, wherein an augmentation pin may be either provided in the distal implant portion of the elongated housing or in the augmentation screw which can be coupled to the distal implant portion. Only steps S2, S4 and S6 may be omitted in case more than one augmentation pin is to be used.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

LIST OF REFERENCE SIGNS

100 Handling device
110 Housing
120 Axial through-bore
130 Lateral opening
140 Distal implant portion
150 Proximal tool portion
160 Locking element
170 Projection
200 Pin-magazine
210 Grip portion
220 Body
230 Recess
240 Notch
250 Chamfer
260 Pin-retainer
300 Augmentation screw
322, 324 Lateral bore
330 Proximal end portion
340 Outer thread
00 Augmentation pin 410 Closing plug
412 Rib
414 Recess
416 Tapered end portion
500 Driving tool
600 Ultrasonic applicator
610 Sonotrode
612 Tip of sonotrode
614 Section with reduced diameter

The invention claimed is:

1. A device for handling and implanting an augmentation implant, comprising:
an augmentation screw;
a plurality of polymeric augmentation pins;
an augmentation pin magazine comprising a plurality of pin-retainers for retaining the plurality of polymeric augmentation pins therein;
an ultrasound applicator comprising an ultrasound transducer and a sonotrode for engaging the plymeric augmentation pins;
an elongated housing having a distal portion, a proximal tool portion and a body portion extending along a second longitudinal axis and connecting the distal portion to the proximal tool portion, said elongate housing includes an axial through-bore extending through the proximal tool portion, the body portion and the distal screw portion of the elongated housing for accommodating the sonotrode of the ultrasound applicator for engaging the augmentation pins, and a lateral opening extending through the body portion of the elongate housing for receiving the augmentation pin magazine, wherein the axial through-bore and the lateral opening intersect each other;
wherein the distal portion distal of the housing lateral opening engages a proximal end of the augmentation screw, such that the axial through bore of the elongated housing is aligned with an axial through bore of the augmentation screw;
a closing plug insertable into the axial through bore of the augmentation screw and having a plurality of ribs on a proximal end forming channels, wherein when the closing plug is disposed within the axial bore of the augmentation screw the plug closes the axial through bore of the augmentation screw at a distal tip of the augmentation screw, and the channels are configured to redirect fluidized polymeric pins from the axial bore and out of at least one lateral through bore in the augmentation screw;
a tool mounted on a proximal portion of the housing for driving the augmentation screw, such that the distal housing portion is configured to transmit torque from the tool mounted on the proximal end of the elongated housing to the augmentation screw, for screwing in the augmentation screw into an object;
wherein the elongate housing lateral opening has a locking system for holding the pin magazine therein; and
the lateral opening having a projection for engaging an augmentation pin and wherein the locking system has a locking element for engaging the pin magazine to align the augmentation pin with the axial through-bore in the elongate housing for inserting the augmentation pin into the axial through bore of the augmentation screw, when the augmentation pin is located in the pin-retainer;
wherein the sonotrode is slidably and at least partially accommodated in the axial through-bores of the elongated housing and the augmentation screw when the elongated housing is connected to the augmentation screw, such that when the augmentation pin magazine is placed and locked in the lateral opening and at least one of the augmentation pins is aligned with the axial through-bore of the elongated housing, then the aligned augmentation pin is pushed by the sonotrode through at least a portion of the axial through-bore of the elongated housing, out of the housing and into the axial bore of the augmentation screw, and then fluidized within the axial bore of the augmentation screw due to ultrasound vibrations generated from the ultrasound transducer, then pressed out through the at least one lateral through bore of the augmentation screw, the at least one lateral through bore extending through a body portion of the augmentation screw and in fluid communication with the axial bore of the augmentation screw; and
wherein the augmentation pin magazine is configured to be further inserted and locked in the lateral through opening of the housing to align a second one of the retained polymeric augmentation pins with the axial through bore of the elongated housing to be prepared to be pushed by the sonotrode into the axial bore of the augmentation screw.

2. The handling and implanting device of claim 1, wherein the locking element blocks lateral movement of the augmentation pin when the augmentation pin is placed in the housing lateral opening and is aligned with the axial through-bore.

3. The handling and implanting device of claim 2, wherein the elongated housing projection projects into the lateral opening engaging the augmentation pin, so that the augmentation pin is automatically aligned with the axial through-bore, when the augmentation pin is placed in the lateral opening and engages the projection.

4. The handling and implanting device of claim 1, wherein the ultrasound applicator is arranged so that the sonotrode extends from the ultrasound transducer in a direction towards the distal portion of the housing.

5. The handling and implanting device of claim 4, wherein a proximal tool portion is adapted for releasably connecting the ultrasound applicator at the elongated housing.

6. The handling and implanting device of claim 5, wherein the tool has a distal driving end, wherein the distal driving end is adapted to be coupled to the proximal tool portion when the ultrasound applicator is released from the proximal tool portion.

* * * * *